US008024282B2

(12) United States Patent
Tsypin et al.

(10) Patent No.: US 8,024,282 B2
(45) Date of Patent: Sep. 20, 2011

(54) METHOD FOR RELIABLE CLASSIFICATION OF SAMPLES IN CLINICAL DIAGNOSTICS USING AN IMPROVED METHOD OF CLASSIFICATION

(75) Inventors: Maxim Tsypin, Steamboat Springs, CO (US); Heinrich Röder, Steamboat Springs, CO (US)

(73) Assignee: Biodesix, Inc., Broomfield, CO (US)

( * ) Notice: Subject to any disclaimer, the term of this patent is extended or adjusted under 35 U.S.C. 154(b) by 682 days.

(21) Appl. No.: 12/218,519

(22) Filed: Jul. 15, 2008

(65) Prior Publication Data
US 2008/0306898 A1  Dec. 11, 2008

Related U.S. Application Data

(63) Continuation-in-part of application No. 11/396,328, filed on Mar. 31, 2006, now Pat. No. 7,736,905.

(60) Provisional application No. 60/959,990, filed on Jul. 18, 2007.

(51) Int. Cl.
 G06F 17/00 (2006.01)
 G06N 5/02 (2006.01)
 G01N 33/48 (2006.01)
(52) U.S. Cl. ............................... 706/47; 436/64
(58) Field of Classification Search ............ 706/47
 See application file for complete search history.

(56) References Cited

U.S. PATENT DOCUMENTS

| 6,003,027 | A | 12/1999 | Prager | 707/5 |
| 7,016,884 | B2 | 3/2006 | Platt et al. | 706/20 |
| 7,228,239 | B1 | 6/2007 | Cetto | 702/30 |
| 7,359,805 | B1 | 4/2008 | Cetto | 702/30 |
| 2005/0048547 | A1* | 3/2005 | Zhao et al. | 435/6 |

(Continued)

FOREIGN PATENT DOCUMENTS
WO  WO 2004/038602  5/2004
(Continued)

OTHER PUBLICATIONS

Petty, Russell, Keith Kerr, Graeme Murray and Marianne Nicolson et al. "Tumor Transcriptome Reveals the Predictive and Prognostic Impact of Lysosomal Protease Inhibitors in Non-Small-Cell Lung Cancer" Journal of Clinical Oncology. vol. 24, No. 11, Apr. 10, 2006.*

(Continued)

Primary Examiner — Kakali Chaki
Assistant Examiner — Ben M Rifkin
(74) Attorney, Agent, or Firm — McDonnell Boehnen Hulbert & Berghoff LLP (57) ABSTRACT

A system for classification of a test object using a training set comprising a plurality of objects, each of which is assigned as a member of a class. Collectively, the objects in the training set are members of at least two classes. A computer system is configured as a probabilistic classifier. The classifier estimates the probability of the test object being a member of each of the classes in the training set. The probabilistic classifier estimates the probability with reference to the class assignments of the objects in the training set which are neighbors to the test object within a defined region within the training set. The probabilistic classifier takes into account the situation in which there is an imbalance in the number of objects in the different classes in the training set. Additionally, the probabilistic classifier does not require any knowledge of the probability distribution function of the classes in the training set.

34 Claims, 2 Drawing Sheets

U.S. PATENT DOCUMENTS

| | | | |
|---|---|---|---|
| 2005/0164218 A1 | 7/2005 | Agus et al. | |
| 2006/0195269 A1* | 8/2006 | Yeatman et al. | 702/20 |
| 2007/0231921 A1 | 10/2007 | Röder et al. | 436/173 |

FOREIGN PATENT DOCUMENTS

| | | |
|---|---|---|
| WO | 2005/098445 | 10/2005 |

OTHER PUBLICATIONS

*Handbook of Mathematical Functions,* Ed. M. Abramowitz et al., Dover NY (1965) Chapter 15, pp. 556-557.

E. Fix and J. L. Hodges, "Discriminatory analysis. Nonparametric discrimination: consistency properties." Report No. 4, Project No. 21-49-004, USAF School of Aviation Medicine, Randolph Field, Texas (Feb. 1951) Reprinted in International Statistical Review, 57 238-247 (1989).

E. Fix and J. L. Hodges, "Discriminatory analysis. Nonparametric discrimination: small sample performance", Report No. 11, Project No. 21-49-004, USAF School of Aviation Medicine, Randolph Field, Texas (Aug. 1952).

T. M. Cover and P. E. Hart, "Nearest Neighbor Pattern Classification", IEEE Transactions on Information Theory, vol. IT-13, pp. 21-27(1967).

B. W. Silverman and M. C. Jones, "E. Fix and J. L. Hodges (1951): An important contribution to nonparametric discriminant analysis and density estimation", International Statistical Review, 57, 3, pp. 233-238 (1989).

J. Wang, P. Neskovic and L. N. Cooper, "Partitioning a feature space using a locally defined confidence measure", ICANN/ICONIP, pp. 200-203 (2003).

J. Wang, P. Neskovic and L. N. Cooper, "An adaptive nearest neighbor algorithm for classification", Proceedings of the 4th International Conference on Machine Learning and Cybernetics, Guangzhou, Aug. 18-21, pp. 3069-3074 (2005).

J. Wang, P. Neskovic and L. N. Cooper, "Neighborhood size selection in the $k$-nearest-neighbor rule using statistical confidence", Pattern Recognition 39, pp. 417-423 (2006).

X.-J. Ma, R. Patel, X. Wang, et al, "Molecular classification of human cancers using a 92-gene real-time quantitative polymerase chain reaction assay", Arch. Pathol. Lab. Med., vol. 130 pp. 465-473 (2006).

Robert P.W. Duin, David M.J. Tax, "Classifier Conditional Posterior Probabilities", published in: A. Amin, D. Dori, P. Pudil, and H. Freeman (eds.), *Advances in Pattern Recognition,* Lecture Notes in Computer Science, vol. 1451, p. 611-619, Springer, Berlin (1998), ISBN 978-3-540-64858-1.

D. Coomans and D.L. Massart, "Alternative $k$-Nearest Neighbour Rules in Supervised Pattern Recognition", Part 1, Analytica Chimica Acta, 136, pp. 15-27 (1982).

Reyzer, Michelle L. et al., "MALDI mass spectrometry for direct issue analysis: a new tool for biomarker discovery," Juornal of Proteome Research, 4(4):1138-1142 (Jul. 2005).

Bhanot, Gyan et al., "A robust meta-classifcation strategy for cancer detection from MS data," Proteomics, 6 (2):592-604 (Jan. 2006).

Everson, R.M. et al., "A variable metric probabilistic k-nearest-neighbours classifier," Intelligent Data Engineering and Automated Learning—Ideal 2004. 5th International Conference. Proceedings (Lecture Notes in Comput. Sci. vol. 3177) 654-659 (2004).

European Search Report for Application No. EP 10 00 3344 dated Aug. 19, 2010.

* cited by examiner

METHOD FOR RELIABLE CLASSIFICATION OF SAMPLES IN CLINICAL DIAGNOSTICS USING AN IMPROVED METHOD OF CLASSIFICATION

CROSS-REFERENCE TO RELATED APPLICATIONS

This application claims priority benefits under 35 U.S.C. §119 to U.S. provisional application Ser. No. 60/959,990 filed Jul. 18, 2007.

This application also claims priority benefit under 35 U.S.C. §120 as a continuation-in-part of U.S. patent application Ser. No. 11/396,328 filed Mar. 31, 2006, published as U.S. Patent Application publication 2007/0231921, pending.

The entire content of the Ser. No. 60/959,990 filed Jul. 18, 2007 and Ser. No. 11/396,328 filed Mar. 31, 2006 is incorporated by reference herein.

BACKGROUND

This disclosure is related to the field of methods and systems which perform classification of an object, such as a data set associated with a test sample. Here and in the following, the term "classification" is used in the sense of supervised classification, i.e. classification based on a training set of previously labeled objects. More particularly, the disclosure is directed to a method for determining the probability that a test object is a member of a particular class, given a training set of previously labeled objects. The methods have many possible applications, including medical-related fields. For example, the classification methods can be used for predicting whether a patient will derive benefit or adverse effects from the administration of a particular drug.

The present disclosure discusses one possible application of the invention in which a test object to be classified is in the form of a mass spectrum containing a peak, or a group of peaks, with respect to a training set comprising a set of mass spectra that are members of two or more classes. However, the methods can be used with other types of data. Hence, in the following disclosure, the term "test instance" is occasionally used to represent the object to be classified, which may take the form of a mass spectrum containing a peak, or a group of peaks, or other form of data, e.g., data from a different type of analytical instrument, e.g., gas chromatograph or spectrometer. The term "instance" is used as synonymous to "object".

Of the various classification methods known in the art, the k-Nearest Neighbor (kNN) method is a powerful method of nonparametric discrimination, or supervised learning. Background literature related to the kNN method includes E. Fix and J. L. Hodges, "Discriminatory analysis. Nonparametric discrimination: consistency properties." Report Number 4, Project Number 21-49-004, USAF School of Aviation Medicine, Randolph Field, Tex. (February 1951). Reprinted in *International Statistical Review*, 57 (1989) 238-247; E. Fix and J. L. Hodges, "Discriminatory analysis. Nonparametric discrimination: small sample performance." Report Number 11, Project Number 21-49-004, USAF School of Aviation Medicine, Randolph Field, Tex. (August 1952); T. M. Cover and P. E. Hart, "Nearest Neighbor Pattern Classification", *IEEE Transactions on Information Theory*, IT-13 (1967) 21-27; and B. W. Silverman and M. C. Jones, "E. Fix and J. L. Hodges (1951): An important contribution to nonparametric discriminant analysis and density estimation", *International Statistical Review*, 57 (1989) 233-238.

Each object, or instance, to be classified is characterized by d values $x_i$, $i=1 \ldots d$ and is thus represented by a point in a d-dimensional space. In the example of mass spectrometry (MS) data, each value $x_i$ represents an intensity of an individual feature, or intensity of an individual peak, in the mass spectrum. The distance between any two instances can be defined in different ways, the simplest of which is the usual Euclidean metric $\sqrt{\Sigma_i(x_i-x'_i)^2}$., but any other distance measure can also be used. Given a training set (a set of instances with known class assignments/labels) and a positive integer k, classification of the test object is performed as follows.

1. Find the k nearest neighbor instances from the training set instances to the test object.
2. Determine which of the labels of the k nearest neighbor training set instances is in the majority.
3. Assign the label determined as being in the majority in step (2) to the test object.

This simple algorithm has two noticeable drawbacks. First, it does not properly take into account the number of instances of each class in the training set. Simply adding more instances of a given class to the training set would bias classification results in favor of this class. Thus, the algorithm in the above simple form is only applicable when each class in the training set is represented by an equal number of instances. In practice, this is rarely the case.

Second, the algorithm provides no information on the confidence of class assignment for individual instances. Consider, for example, the case of k=15 and two classes. It is intuitively clear that the confidence of class assignment in the situation where all 15 of the nearest neighbors belong to the same class is much higher than in the situation where 8 belong to one class and 7 belong to another class. In many applications, such as those related to clinical diagnostics, it may be very important to be able to characterize the confidence of each individual class assignment.

In this document, we address these problems by providing a probability estimate of the test instance belonging to each of the classes in the training set, based on the class labels of each of the k nearest neighbors from the training set. An example is described below where there are two classes of objects in the training set, however the methods can be extended to the situation where there are three or more classes. We provide two derivations of the probability estimates, one within the kernel density estimation framework (a fixed vicinity of the test instance determines the number of neighbors), the other within the kNN framework (a fixed number of neighbors determines the size of the vicinity). Both lead to the same result for the probability estimate of the test instance belonging to each of the classes.

Unlike the estimates of the overall error rate of kNN classification that depend on the probability distributions associated with the classes, the probability estimates of this disclosure provides a reliability of class assignment for each individual test instance, depending only on the (known) training set data and their labels. It also properly accounts for complications arising when the numbers of training instances in the two classes are different, i.e. $N_1 \neq N_2$. Here $N_1$ and $N_2$ are the numbers of instances in the training set that belong, respectively, to class 1 and to class 2, if one considers the two class classification problems. Extensions to more than two classes are analogous.

The problem of statistical confidence of kNN classification has been also addressed in several other references, including see J. Wang, P. Neskovic and L. N. Cooper, "Partitioning a feature space using a locally defined confidence measure", ICANN/ICONIP (2003) 200-203; J. Wang, P. Neskovic and L. N. Cooper, "An adaptive nearest neighbor algorithm for classification", Proceedings of the 4th International Conference on Machine Learning and Cybernetics, Guangzhou (2005) 3069-3074; J. Wang, P. Neskovic and L. N. Cooper, "Neighborhood size selection in the k-nearest-neighbor rule using statistical confidence", *Pattern Recognition* 39 (2006) 417-423; and X.-J. Ma, R. Patel, X. Wang, et al, "Molecular classification of human cancers using a 92-gene real-time quantitative polymerase chain reaction assay", *Arch. Pathol. Lab. Med.* 130 (2006) 465-473. However, the "confidence level" proposed in the J. Wang et al. papers has a completely different statistical meaning and cannot be used to estimate the reliability of class assignment for each individual test instance. The same is true for P-values discussed in the Ma et al. paper at p. 466.

Additional prior art of interest includes the paper of Robert P. W. Duin, David M. J. Tax, *Classifier Conditional Posterior Probabilities*, published in: A. Amin, D. Dori, P. Pudil, and H. Freeman (eds.), *Advances in Pattern Recognition*, Lecture Notes in Computer Science, Volume 1451, p. 611-619, Springer, Berlin (1998), ISBN 978-3-540-64858-1. Other prior art of interest includes U.S. Pat. Nos. 7,016,884, 7,359,805, 7,228,239, and 6,003,027.

The probabilistic classification methods and system of this disclosure provide a facility for determining the reliability of class assignment for each individual test instance. The methods depend only on the (known) training set data, and are not dependent on knowledge of the probability density functions of the training set data, i.e., they are non-parametric. They also avoid the potential bias in a classification system when the numbers of instances in the two classes in the training set are different.

SUMMARY

In one aspect, a method is disclosed for classifying a data set. The data set may take the form of a mass spectrum containing one or more peaks, or other format of data.

The method includes a step of accessing a machine readable memory storing a training set comprising a number of data sets. Each of the data sets in the training set has a known class label. Collectively, the data sets in the training set are members of at least two classes, e.g., Class 1 and Class 2. The meaning of the class assignments to the data sets in the training set will of course depend on the application. In one example, data sets of "normal" patients are assigned as "class 1" and data sets of patients having a particular medical condition, e.g., cancer, are assigned as "class 2". As another example, data sets of patients which derive benefit from treatment for a disease by a particular family of drug compounds are assigned membership in class 1 whereas data sets of patients which do not derive benefit, or suffer adverse effects from treatment with the family of drug compounds are assigned membership in class 2.

The method further includes a step of estimating the probability of the test instance as being a member of each of the classes in the training set. This probability estimate is reflected by a number between 0 and 1. The higher the number, the greater the probability is that the test instance is a member of the assigned class. Various methods for calculating this probability estimate are described, including calculations and approximations for use where the number of test data points in the training set in the different classes is not the same.

The estimating of probability is performed with reference to the class assignments of a group of data sets in the training set which are neighbors to the test instance. These neighbors are located within a certain defined region within the training set. This defined region may be expressed as all those test data points within a sphere centered on the test instance to be classified (parameter ω described below), or as a given number of k data points which are closest to the test instance, according to the distance measure being used. In this example, k can take any integer value greater than or equal to one, and can be either an even or an odd number.

The method then classifies the test instance as belonging to the class with the highest estimated probability.

In some embodiments, the method may also include the step of comparing the estimates of probabilities for each of the classes to determine if the probability difference between the class having the highest probability estimate and the class having the next highest probability estimate is greater than a user-supplied parameter (p-diff below). For example, this user-supplied parameter can be 0.1. When the probability difference between the class with the highest probability and the class with the second highest probability is 0.1 or greater, then the classification is maintained. If the difference is less that 0.1, then the classifier returns a result such as "undefined" or "unable to classify."

When the training set includes instances being members of two classes, the probability of the test instance being a member of Class 1 is estimated according to the relation:

$$P(\text{class } 1) = \frac{k_1 + 1}{k_1 + k_2 + 2} \cdot {}_2F_1\left(1, k_2+1; k_1+k_2+3; 1-\frac{N_1}{N_2}\right).$$

where $_2F_1(1, k_2+1; k_1+k_2+3; 1-N1/N2)$ is a calculation of the hypergeometric function $_2F_1$. $N_1$ is the number of objects in the training set in the first class, and $N_2$ is the number of objects in the training set in the second class. Also, in this expression, $k_1$ represents the number of neighbors of class 1 within the defined region and $k_2$ represents the number of neighbors in class 2 within the defined region. This expression can be used to calculate the probabilities that the test instance is a member of each of the two classes in the situation where $N_1$ is equal to $N_2$, and where $N_1$ is not equal to $N_2$.

For the situation in which there are more than two classes and sample sizes in the training set are different (i.e., the numbers $N_i$ of objects in each of the classes in the training set are not necessarily the same), it is difficult to obtain p(class i) in closed form. In this case, the following much simplified estimate may be used:

$$\frac{p(\text{class } i)}{p(\text{class } j)} = \frac{(k_i+1)}{(k_j+1)} \cdot \frac{N_j}{N_i}$$

Or, equivalently, each p(class i) is proportional to $$\frac{1}{N_i}(k_i+1), \text{ while } \sum_{i=1}^{N \text{ classes}} p(\text{class } i) = 1.$$

In one example of a diagnostic application of this invention, the test data sets take the form of test data (e.g., mass spectrometry (MS) data from serum samples) obtained from two classes of patients: 1) a first class of patients exhibiting an adverse health condition (e.g., cancer or other disease) and 2) a second class of patients that do not share the adverse health condition. The classes assigned to the data sets in the training set correspond to the two classes of patients. The test instance represents test data obtained from a patient, e.g., MS data from a serum sample of a patient, and information is desired as to whether the patient falls into the first or second class. The methods of this disclosure provide a way of quantitatively determining the probability that the test instance falls into class 1 or class 2.

As another example in the diagnostics arena, the data sets in the training set are obtained from two classes of patients: 1) a first class of patients that derive benefit from a particular therapy for treatment of a health condition and 2) a second class of patients that do not derive benefit, or suffer adverse effects from the particular therapy for treatment of the health condition, and wherein the classes assigned to the data sets correspond to the two classes of patients. In one example, the health condition comprises cancer.

In another aspect, a system is provided for performing a classification of a test instance. The system includes a machine-readable memory storing a training set comprising a plurality of data sets. Each of the data sets in the training set is assigned as a member of a class, and collectively the data sets in the training set form at least two classes. The system further includes a computer system. The computer system may be embodied in any convenient form such as a general purpose computer having a memory storing software instructions for execution by a processing unit. The computer system is configured, e.g., with hardware and software as described below, as a probabilistic classifier. The classifier estimates the probability of the test instance as being a member of a class in the training set. The module estimates the probability with reference to the class assignments of data sets in the training set which are neighbors to the test instance within a defined region within the training set. This defined region may be expressed as all those test data points within a sphere centered on the test instance to be classified (parameter ω described below), or as a given number of k data points which are closest to the test instance. In this example, k can take any integer value greater than or equal to one.

BRIEF DESCRIPTION OF DRAWINGS

FIGS. 3 and 4 illustrate the situation where the instances in the training set can be represented by points in two-dimensional space, and the Euclidean measure is used for the distance between instances. The methods of this disclosure can be applied to trainings sets which are not capable of being represented in a two-dimensional space, and thus FIGS. 3 and 4 are offered by way of example and not limitation.

DETAILED DESCRIPTION

The probabilistic classifier features of this disclosure will be described in greater detail later in this document. To fully understand how the classifier can be implemented in a diagnostic environment, this disclosure will describe the invention in the context of classifying a mass spectrometry data obtained from a patient serum sample.

I. Overview of Diagnostic Application of a Probabilistic Classifier

In the application U.S. 2007/0231921, the inventors of the instant invention disclosed a novel method of determining if a patient will derive benefit from a treatment by testing a sample of the patient (e.g., a serum sample) by mass spectroscopy. As an example of one embodiment of this invention, the inventors have applied their technique to a cancer, Non-Small-Cell Lung Cancer (NSCLC). Non-Small-Cell Lung Cancer is a leading cause of death from cancer in both men and women in the United States.

Treatment of NSCLC has been relatively poor over the years. Chemotherapy, the mainstay treatment of advanced cancers, is only marginally effective, with the exception of localized cancers. While surgery is the most potentially curative therapeutic option for NSCLC, it is not always possible depending on the stage of the cancer.

Recent approaches for developing anti-cancer drugs to treat the NSCLC patients focus on reducing or eliminating the ability for cancer cells to grow and divide. These anti-cancer drugs are used to disrupt the signals to the cells to tell them whether to grow or die. Normally, cell growth is tightly controlled by the signals that the cells receive. In cancer, however, this signaling goes wrong and the cells continue to grow and divide in an uncontrollable fashion, thereby forming a tumor. One of these signaling pathways begins when a chemical in the body, called epidermal growth factor, binds to a receptor that is located on the surface of many cells in the body. The receptor, known as the epidermal growth factor receptor (EGFR) sends signals to the cells, through the activation of an enzyme called tyrosine kinase (TK) that is found within the cells.

Two anti-cancer drugs that were developed and prescribed to the NSCLC patients are called gefitinib (trade name "Iressa") and erlotinib (trade name "Tarceva"). These anti-cancer drugs target the EGFR pathway and have shown promise in being effective toward treating NSCLC cancer. Iressa and Tarceva inhibit the enzyme tyrosine kinase that appears to be important to the growth of cancer cells. Iressa has been used as a single agent of the treatment of NSCLC that has progressed after, or failed to respond to, two other types of chemotherapies.

However, only between 10% and 20% of patients in Caucasian populations derive benefit from Iressa, and this has led to withdrawal of Iressa as a second-line treatment. Surprisingly, the percent of patients deriving benefit from Iressa in Asia has been considerably higher and Iressa is stilled used. Traceva is still approved and routinely given to patients, but still has response rate concerns. While it appears that Iressa and Traceva have the ability to be effective in some patients, they may not be drugs effective in treating all patients. There may be many factors involved in a patient's ability to derive benefit from these drugs that are currently unknown. However, if the method existed that could be used to predict the effectiveness of these anti-cancer drugs for individual NSCLC patients, doctors could then prescribe these drugs to those patients predicted to derive benefit from the anti-cancer drugs.

Our application U.S. 2007/0231921 discloses a diagnostic test to determine whether a patient will derive benefit from these drug treatments. The determination is made by measuring the intensity of a predefined set of peaks in a spectrum produced by a mass spectrometer from serum extracted from a patient's blood. The mass spectrometer produces a spectrum having certain peaks that that can be utilized to compare with spectra produced from serum of patients that derived benefit, or did not derive benefit from the drug treatments. It is often not necessary to actually determine what chemical compound or compounds determine the intensity of the peak. The intensities of a carefully chosen set of peaks in the mass spectrum can by themselves characterize the treatment potential for the drug in a specific patient.

The method includes obtaining a test spectrum produced by a mass spectrometer from a serum of a patient. The test spectrum ("test instance" herein) is classified relative to a training set in the form of a group of class labeled spectra produced from respective serum from other patients at the same or similar clinical stage disease or disorder and known to have derived benefit, or not derived benefit from the drug. The methods of this disclosure can be used in this classification.

The classification methods of this disclosure are implemented as a test procedure, wherein a patient serum (or plasma) sample is obtained, subjected to mass spectrometry and then the mass spectrum is classified with the probabilistic classifier of this disclosure. The classifier makes use of the training set. The manner in which this training set is obtained is explained in our application U.S. 2007/0231921 and only a brief overview will be described in this document in order to not obfuscate the present disclosure.

Figure 1:
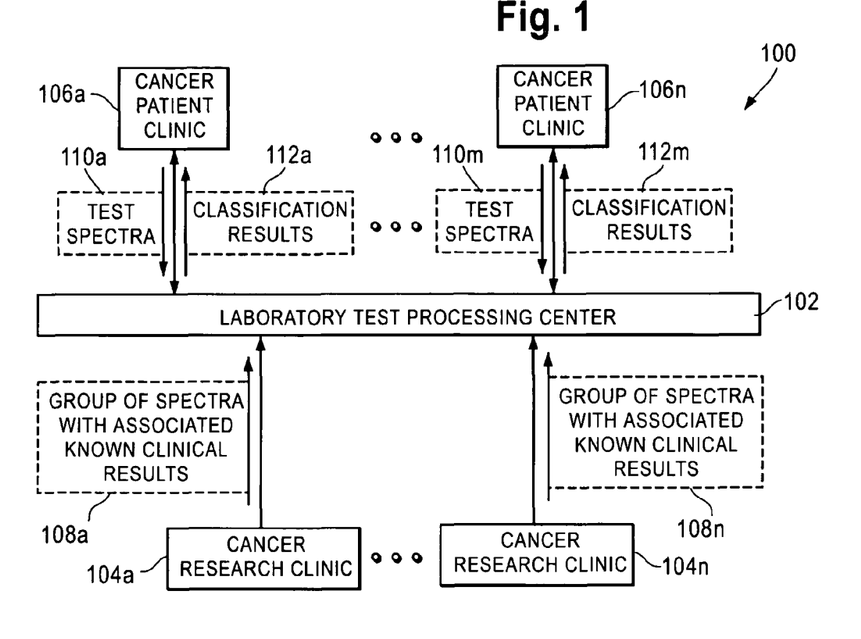
FIG. 1 is a block diagram showing a laboratory test processing center, cancer research clinics and cancer patient clinics. The probabilistic classification methods and system are typically, but not necessarily, implemented in a computer system and associated machine-readable memory storage, or database located in the laboratory test processing center.

FIG. 1 is a block diagram of an exemplary relationship between a laboratory test processing center 102, cancer research clinics 104a-104n (collectively 104), and cancer patient clinics 106a-106m (collectively 106). The laboratory test processing center 102 operates to process tests from cancer research clinics 104 and cancer patient clinics 106. In one embodiment, the cancer research clinics 104 and cancer patient clinics 106 are part of the same organization, such as a hospital. The cancer research clinics 104 perform drug trials and testing to determine effectiveness of certain drugs to treat patients. For example, some patients with non-small-cell lung cancer derive benefit from particular anti-cancer drugs, and some patients do not. These anti-cancer drugs may include gefitinib and erlotinib that target the epidermal growth factor receptor pathway. During clinical studies and non-clinical studies, the cancer research clinics 104 determine whether, and to what extent, each patient derives benefit, or suffers from the adverse reaction, from the anti-cancer drug.

The cancer research clinics 104 may be any facility that performs clinical studies or otherwise administers cancer medications to cancer patients and monitors effectiveness of the medications. The cancer research clinics 104 may take blood samples and process them to produce blood plasma (the liquid component of blood from which blood cells are removed) or serum, which is blood plasma having clotting factors, such as fibrin, removed. The serum or plasma may be processed and used to produce a spectrum by a mass spectrometer so that the peaks in the spectrum can be detected. In one embodiment, the mass spectrometer is a time-of-flight (TOF) mass spectrometer that uses matrix-assisted laser desorption/ionization (MALDI). The spectrum may include surrogate markers or peaks within the spectrum indicative of certain chemicals or matter within the serum or plasma.

Continuing with FIG. 1, as a result of the treatment of the patients, effectiveness of the anti-cancer drugs being administered to each patient may be recorded and observed. The laboratory test processing center 102 receives mass spectral data derived from the samples obtained from the patients, together with associated known clinical results 108 from the cancer research clinics. These mass spectra constitute the training set. Each spectrum in the training set is given a label "Good" or "Poor" according to the known clinical result for the corresponding patient. Label "Good" means that the patient derived benefit from the treatment, while label "Poor" means that the patient did not derive benefit, or experienced adverse effects from the treatment. After the training set has been obtained, the laboratory test processing center 102 can perform classification of the test samples. The laboratory test processing center 102 receives test spectra 110a-110m (collectively 110) from cancer patient clinics 106 and performs analysis on these test spectra 110 to determine which class each test spectrum (i.e., each patient) is most likely to belong to. Alternatively, rather than receiving mass spectra, the laboratory test processing center 102 may receive blood samples or serum samples to process and produce the mass spectra for processing and classification.

Once the laboratory test processing center 102 has classified the test spectrum 110, and optionally makes the determination as to whether the cancer patient is likely to derive benefit from the anti-cancer drug, classification results 112a-112m (collectively 112) may be delivered to the respective cancer patient clinic 106. In one embodiment, the classification results are class labels produced by a classifier function as further described herein below.

Although shown separately, the laboratory test processing center 102 may be part of the cancer research clinics 104 or cancer patient clinics 106. In one embodiment, the laboratory test processing center 102 is functionally incorporated into test equipment, such as a mass spectrometer or processing system operating in conjunction with the test equipment. Alternatively, the functionality may be incorporated onto a computer system or other processing system that is configured to perform the various processing utilized in processing and classifying the spectra and not part of or associated with the test equipment. For example, the computer system may be a server operated by the laboratory test processing center 102, clinic research clinic 104, and/or cancer patient clinic 106. Although FIG. 1 describes cancer clinics, it should be understood that these clinics may be common clinics or clinics specific to a particular disease or illness.

Figure 2:
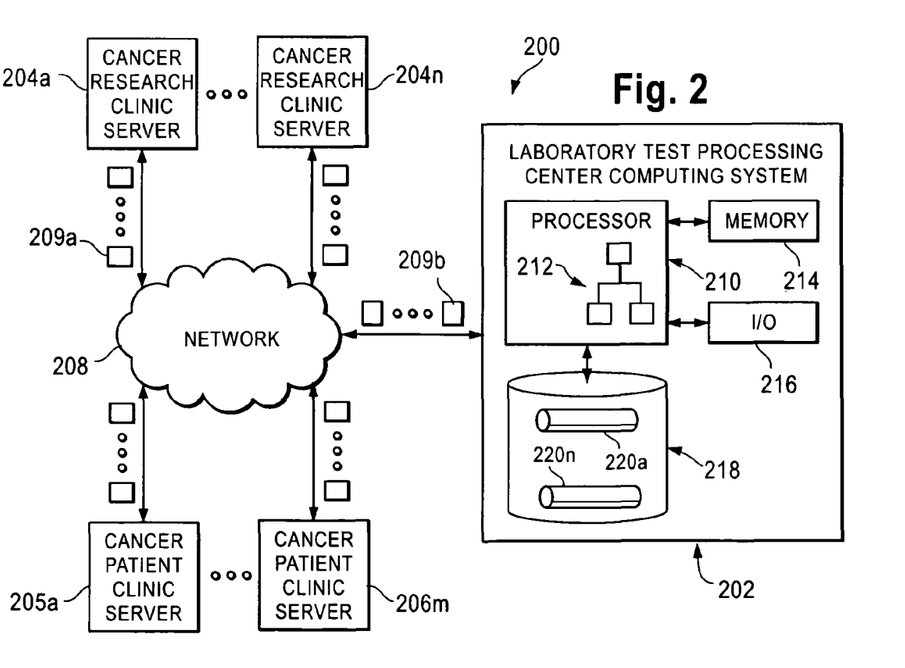
FIG. 2 is a block diagram showing a system for communication and processing information between the test processing center, cancer research clinics and cancer patient clinics of FIG. 1.

FIG. 2 is a block diagram of an exemplary system 200 for communicating and processing information between the laboratory test processing center 102, cancer research clinics 104, and cancer patient clinics 106 of FIG. 1. A laboratory test processing center computing system 202 may be operated by the laboratory test processing center 102. Cancer research clinic servers 204a-204n (collectively 204) may be operated by the cancer research clinics 104 and cancer patient clinic servers 206a-206m (collectively 206) may be operated by the cancer patient clinics 106. Each of the computing system 202 and servers 204 and 206 may communicate over network 208 via digital data packets 209a-209b or other communication technique as understood in the art. The network 208 may be the Internet or other public or non-public communication network.

The laboratory test processing center computing system 202 may include a processor 210 executing software 212 for processing the mass spectra to determine classifications of all or a portion thereof in accordance with the principles of the present invention as described further below. The computing system 202 may further include memory 214, in which the software 212 may reside when being executed, input/output (I/O) unit 216, which may perform the communication over the network 208, and machine-readable memory storage device 218 to which the processor 210 communicates. The storage device 218 may include one or more databases 220a-220n (collectively 220) in which the mass spectra, and other related data is stored to enable the laboratory test processing center 102 to determine whether a cancer patient is likely to derive benefit from an anti-cancer drug. The storage device 218 may also store mass spectra, peak intensities and other related data directly, without the use of the database. It should be understood that the storage device 218 may include one or more storage devices and located within or external from the computing system 202. It should further be understood that the processor 210 may include one or more processors. Still yet, it should be understood that the computing system 202 may be directly or indirectly in communication with the network 208.

In accordance with FIG. 2, the cancer research clinic servers 204 may communicate spectral data with associated known clinical results to the laboratory test processing center computing system 202. This data, and the data derived from it, constitutes the training set that will be used by the probabilistic classifier. The cancer patient clinic servers 206 may communicate test spectra 110 to the laboratory for the processor 210 to automatically or semi-automatically with the assistance of the scientist or otherwise, classify the test spectra 110 for the cancer patient clinics 106. The laboratory test processing center computing system 202 may process the test spectra 110 and communicate classification results 112 (FIG. 1) back to the cancer patient clinic servers 206. As a result of classifying the test spectra 110, the computing system 202 may store classification results and utilize the results to generate statistical information that may be used for various other purposes, such as efficacy of the anti-cancer drug.

A database, such as database 220 (FIG. 2), or any other appropriate machine-readable storage medium, may be utilized to receive and store differentiating peaks, training sets, mass spectrometer diagnostics, and/or other output parameters from the classification and diagnostic process as described. These parameters may be stored and used for future classification of new spectra from new cancer patients.

Data analysis plays a central role in the discovery of peaks differentiating mass spectra from patients with different clinical outcome and their use either as discovery leads for immuno-histochemical assays or directly in mass spectrometry based diagnosis. Our U.S. Patent application 2007/0231921 discloses developing, testing and analysis procedures for discovery of such peaks. The integrated analysis system includes a number of tools that facilitate the detection of differentiating peaks in the mass spectra, while at the same time providing rigorous tools for the assessment of their significance and validation of the results.

In performing the data analysis, it is generally accepted that cancerous cells have expression levels of specific proteins that are different from those of normal cells. Distinct stages of disease are accompanied by changes in expression levels of specific proteins, e.g., changes in the expression levels of cell-binding proteins in the case of metastatic cancer. In the case of serum samples, and to delineate serum testing from tissue sample testing, it is unlikely that direct tumor excretions are measured due to dilution of these excretions in the blood. The differentiating peaks in serum (or other bodily liquids) samples arise in all likelihood due to a host response reaction dependent on the disease state, such as autoimmune reactions. By detecting differentiating peaks in the spectra, correlation of changes with clinically relevant questions may be performed. To detect differentiating peaks in the spectra of value, independent of their further use, either directly as a diagnostic tool or as leads for immuno-histochemical based testing, the following issues may be addressed during the differentiating peaks discovery process, including the data analysis stage:

Reproducibility: the results of an analysis are to be reproducible. Differentiating peaks are to be repeatably found in the various disease and control groups, and the intensities of these differentiating peaks cannot vary too much within a group. As a simplified measure of reproducibility, coefficients of variations (CV), which have become a standard for assessing diagnostic tests, may be provided by software executed on a processor. The variations of peak intensities within a group, and even within the same sample, may be measured, characterized, and used in downstream analysis and classification.

Robustness: differentiating peaks are to be robust against unavoidable variations in sample preparation and handling, as well as against variations arising from trends in mass spectrometer characteristics. Another reason for patient to patient variability arises from irrelevant differences in the biological state of a patient, for example, the digestive state at the time of sample gathering. Criteria may be developed for distinguishing irrelevant changes from biologically significant ones. In the design of classifiers (i.e., classifier functions or algorithms), which are functions that map from multi-dimensional feature space (e.g., 12 differentiating peaks) to class label space (e.g., "good," "poor," or "undefined") and during feature extraction, real differentiating peaks should not change very much while making small changes to data analysis parameters. Similarly located differentiating peaks should be found in different data sets.

Interpretability: The resulting differentiating peaks may be put in the context of biological interpretability. First, identified differentiating peaks are generally visually noticeable in the mass spectra. The m/z positions of differentiating peaks may give valuable information on the biological relevance of underlying molecules that cause these differentiating peaks. This allows for the interpretation and filtering of the differentiating peaks arising from biologically irrelevant procedures. For example, the measurement of different hemoglobin content of cancerous versus normal samples, may have little or no clinical relevance. In some cases, it may turn out that clinically relevant changes in the spectrum are non-linear combinations of intensities of multiple peaks or features in the spectrum, and are not the simple up/down regulations. Even in this case, the differentiating peaks and/or features in the spectra should be detectable against the noise in the spectra, and the functions with which to evaluate markers should be made explicit.

Sensitivity: Great effort is usually undertaken to gather samples and generate mass spectra. Great care is also taken to avoid missing relevant differentiating peaks or features in the mass spectra, which may result from using data analysis algorithms that are not selective or sensitive enough to actually find these differentiating peaks in a spectrum. For example, if an m/z range is defined as being relevant to a feature, this range is to be broad enough to contain the feature, but should not be too broad to lump in other features present in the spectrum.

The task of comparing mass spectra for the extraction of differentiating peaks is made difficult by the specific nature of these spectra due to intrinsic intensity variations. The ionization probability of individual ions depends on the local sample chemistry (e.g., ion suppression effects). The absolute mass scale can exhibit slight variations from spectrum to spectrum.

Mass spectrometer-specific variations may be measured to reduce or eliminate these variations (in the case of background variations) or to provide measures to assess the relevant significance of signals by estimating the local noise level. It is important to avoid introducing additional variations arising from data preprocessing and analysis. For example, peak picking software that is often bundled with many mass spectrometers has been found to be unreliable to directly use these peaks in a comparative spectral analysis. Early attempts at spectral comparison have instead resorted to using the whole mass spectrum itself in their comparison and classification algorithms. Whole spectra, however, include many thousands of individual data points, most of which are measurements of instrument noise, with only relevant information being confined to the peaks in the mass spectra. As a result, the application of these attempts to classify serum samples has led to exaggerated claims that could not be reproduced in other laboratories.

II. Probabilistic Classifiers

The procedure of classifying a test object (assigning a class label to a test object) in the preferred embodiment uses a probabilistic classifier. The probabilistic classifier is constructed as a result of a supervised learning procedure. Supervised learning is the technique for constructing a classifier from the training data. In one embodiment, the classifier is the mapping from a high-dimensional feature space to label space, i.e. from feature/peak intensities to disease label or response label (otherwise designated as class label). The output of the probabilistic classifier is an estimate of probability, for each class represented in the training set, that the test object belongs to this class. The test object may be subsequently assigned the class label of the class that has the highest associated probability. In one embodiment, a probabilistic k nearest neighbors (KNN) algorithm may be utilized for the classification.

The method includes a step of accessing a machine-readable memory storage 218 or a database 220, (FIG. 2) storing a training set comprising a number of data sets. Each of the data sets in the training set has been previously assigned as a member of a class. Collectively, the data sets in the training set are members of at least two classes, e.g., class 1 and class 2. The meaning of the class assignments to the data sets in the training set will of course depend on the application. In one example, data sets (e.g. mass spectra) of "normal" patients are assigned as "class 1" and data sets of patients having a particular medical condition, e.g., cancer, are assigned as "class 2". As another example, data sets (e.g. mass spectra) of patients which derive benefit from the treatment for a disease by a particular family of drug compounds are assigned membership in class 1 whereas data sets of patients which do not derive benefit from the family of drug compounds are assigned membership in class 2.

In one aspect of this disclosure, the computer system 202 (FIG. 2) implements a module in software and/or hardware for estimating of the probability of the test instance (e.g., test spectrum) as being a member of each class in the training set. The likelihood of correctness of the classification of each individual test instance can be measured by these estimates of probability. The module estimates the probability with reference to the class assignments of data sets in the training set which are neighbors to the test instance within a defined region within the training set. As will be explained below, this region can be defined either in terms of a geometric region ω in the training set centered on the test instance, or in terms of a fixed number of k nearest neighbors in the training set to the test instance. Either approach yields the same general result.

As explained previously, k-Nearest Neighbor (kNN) is a powerful method of nonparametric discrimination, or supervised learning. Each object, or test instance, to be classified, is characterized by d values $x_i$, i=1 ... d and is thus represented by a point in a d-dimensional space. The distance between the two instances can be defined in different ways, the simplest of which is the usual Euclidean metric $\sqrt{\Sigma_i(x_i-x'_i)^2}$, but others can be used without loss of generalizability. Given a training set (a set of instances with known class labels) and a positive integer k, classification of the test instance is performed as follows.

1. Find the k nearest neighbor instances from the training set instances to the test object.
2. Determine which of the training labels of the k nearest neighbor training instances is in the majority.
3. Assign the label determined as being in the majority in step (2) to the test object.

Figure 3:
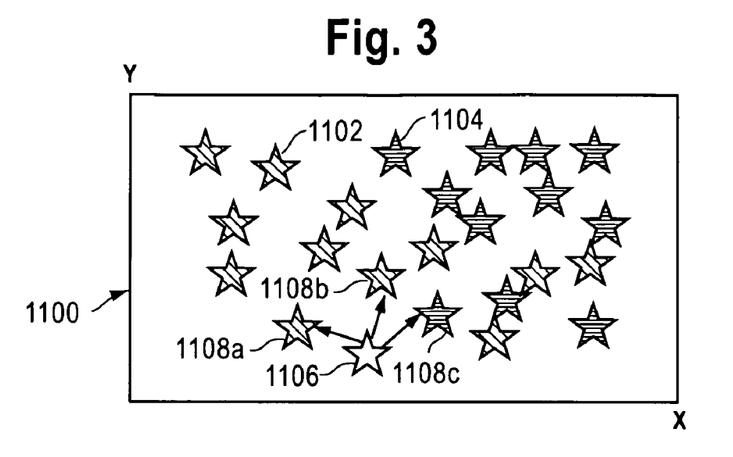
FIG. 3 is a diagram showing a set of instances in a training set belonging to two different classes, and a test instance to be classified by the classifier of this disclosure.

An example of the kNN algorithm will now be explained in conjunction with FIG. 3. FIG. 3 is a graph 1100 showing an exemplary group of class labeled spectra indicia representative of two different classes of patients and a test spectrum instance to be classified. FIG. 3 depicts an example where each spectrum is characterized by two real numbers X and Y, which can be, for example, intensities of the two particular features. In this case each spectrum can be represented by a point in two-dimensional space, as shown in graph 1100 in FIG. 3. If the feature space were a 12-dimensional feature space (i.e., each spectrum were characterized by 12 numbers, e.g. intensities of 12 features or peaks), then it would not be possible to easily graphically represent the spectra, so a two-dimensional feature space is utilized as an example. In practice, the feature space is typically a multi-dimensional space.

In this case, the spectra in the training set are classified with class labels as "good" 1102 and "poor" 1104, where the "good" class labeled spectra indicia 1102 are represented on the graph 1100 as one pattern and the "poor" class labeled spectra indicia 1104 are represented as another pattern. Thus, in this example, there are two classes in the training set, and the objects in the training set belong to either class 1 ("good") or class 2 ("poor"). As previously described, class labeled spectra may be obtained from a cancer research clinic and used as training samples for classification purposes based on the clinical results of a cancer patient treated with an anti-cancer drug, such as Iressa. A test spectrum 1106 to be classified is placed on the graph 1100 in a location representative of a test spectrum from a new cancer patient for whom a treatment plan is being determined. The location of the test spectrum indicia 1106 is based on the amplitudes of the two features (i.e., the x and y amplitudes). As shown, and in accordance with the KNN algorithm, the closest three class labeled spectra indicia 1108a, 1108b, and 1108c will be used to classify the test spectrum 1106 (k=3 in this example). Since among them there are two members in the "good" class 1102, and only one member in the "bad" class 1104, the test spectrum is classified as "good."

The kNN algorithm has two noticeable drawbacks. First, it does not properly take into account the number of objects of each class in the training set, in the case when this number is not the same for every class. In practice there may be many more objects of one class in the training set than for the other class or classes. When the training set is skewed by adding more instances of a given class to the training set, this biases the classification results in favor of this class. Thus, the algorithm in the simple form illustrated in FIG. 3 is only applicable when each class in the training set is represented by an equal number of instances.

Second, the algorithm provides no information on the confidence of class assignment for individual test instances. Consider, for example, the case of k=15 and two classes. It is intuitively clear that the confidence of class assignment in the 15:0 situation is much higher than in the 8:7 situation. In many applications, such as those related to clinical diagnostics, it is very important to be able to characterize the significance of each individual class assignment.

Here we address these problems by providing a probability estimate of the test instance belonging to each of the classes in the training set, based on the class labels of neighbor instances from the training set in a defined region, e.g. each of the k nearest neighbors from the training set. The discussion is presented in the case where the training set consists of objects belonging to two classes, but the principles can be extended to a training set consisting of more than two classes. We provide two derivations, one within the kernel density estimation framework (a fixed vicinity of the test instance determines the number k of neighbors), the other within the kNN framework (a fixed number k of neighbors determines the size of the vicinity). Both lead to the same result for the probability estimate of the test instance belonging to each of the classes.

Figure 4:
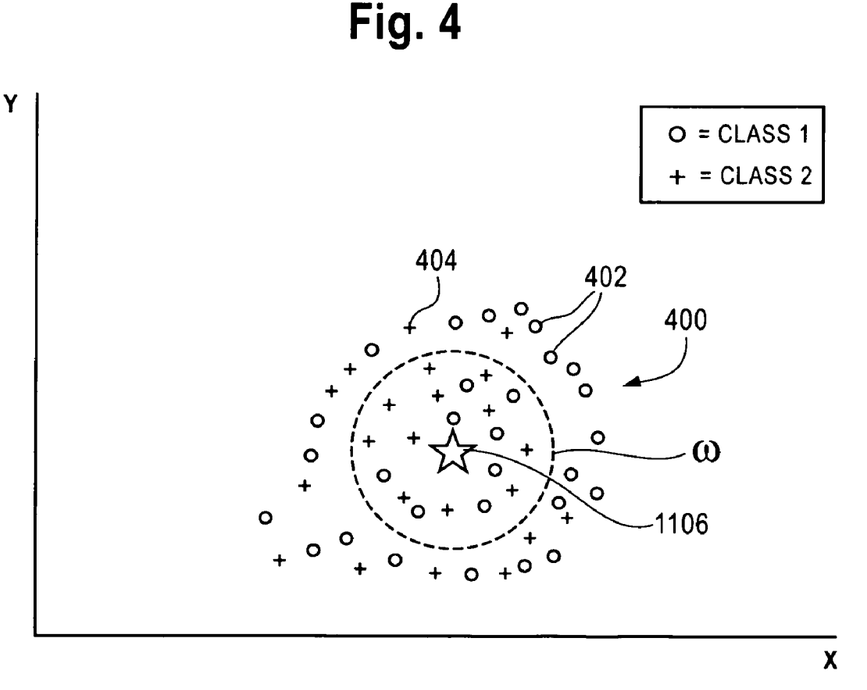
FIG. 4 is a diagram similar to FIG. 3, showing a training set of class labeled spectra of two different classes, a test instance to be classified, and a region of the training set which is used in the probabilistic classifier. This region is shown by parameter ω; however the region can be equivalently represented by a set of k nearest neighbors to the test instance with k being an integer greater than or equal to 1.

FIG. 4 shows a training set 400 composed of a multitude of objects which belong to two classes. The objects belonging to class 1 are shown as small circles 402 and the objects belonging to class 2 are shown by the + symbol, 404. The test instance to be classified is shown by the star 1106. The defined region which is used in the probabilistic classifier can be the k points in the training set which are nearest to the test instance 1106 and contained within a sphere $\omega$ centered on test instance 1106 (the kernel approach below), or by selecting k nearest neighbors (the kNN framework below).

A. Probability Estimate Within the Kernel Approach

Consider the case of two classes in the training set as shown in FIG. 4, which we denote as 1 and 2. Each instance is represented by a point $\vec{x}=(x_1 \ldots x_d)$ in a d-dimensional space. Denote the full d-dimensional space by $\Omega$. Class 1 is characterized by the (unknown) probability distribution $p_1(\vec{x})$, $\int_\Omega p_1(\vec{x})d\vec{x}=1$. Class 2 is characterized by the (unknown) probability distribution $p_2(\vec{x})$, $\int_\Omega p_2(\vec{x})d\vec{x}=1$. The training set consists of $N_1$ points drawn from class 1, and $N_2$ points drawn from class 2. Denote a vicinity of the test point (representing the test instance) by $\omega$. (In case the Euclidean distance is used, $\omega$ is a sphere centered at the test point, see FIG. 4, but this is irrelevant for the following.) For a given realization of the training set, we observe $k_1$ points in $\omega$ from class 1, and $k_2$ points in $\omega$ from class 2.

We make the following assumptions and approximations.
1. Existence of probability densities. As already stated above, the training set is considered to be a sample drawn from the underlying probability distributions with densities $p_1(\vec{x})$ and $p_2(\vec{x})$.
2. Fixed $\omega$. The vicinity $\omega$ of the test point is considered fixed: It can depend on the position of the test point, on the probability distributions from which the training set is drawn, as well as on $N_1$ and $N_2$, but is assumed to stay the same for each realization of the training set.
3. Uniformity within $\omega$. The vicinity $\omega$ is sufficiently small, such that probability densities for the classes, $p_1(\vec{x})$ and $p_2(\vec{x})$, are approximately constant within $\omega$.
4. Poisson approximation. For each class, we make an approximation that the number of training set instances of this class in $\omega$ is drawn from the Poisson distribution. This approximation is valid when $k_i \ll N_i$, $\int_\omega p_i(\vec{x})d\vec{x} \ll 1$, $i=1,2$.

In the Poisson approximation, $k_i$ is drawn from the Poisson distribution with expectation value $\lambda_i$, $$\lambda_i = N_i \int_\omega p_i(\vec{x})d\vec{x}, i=1,2.$$

Assuming equal prior probabilities for class assignment of the test point, that is, P(class 1)=P(class 2)=0.5 in the absence of any information about the neighbors, the probabilities of the test point belonging to class 1 or to class 2 are as follows:

$$\frac{P(\text{class } 1)}{P(\text{class } 2)} = \frac{\int_\omega p_1(\vec{x})d\vec{x}}{\int_\omega p_2(\vec{x})d\vec{x}}.$$

Thus $$P(\text{class } 1) = \frac{\int_\omega p_1(\vec{x})d\vec{x}}{\int_\omega p_1(\vec{x})d\vec{x} + \int_\omega p_2(\vec{x})d\vec{x}} = \frac{\lambda_1/N_1}{\lambda_1/N_1 + \lambda_2/N_2}.$$

Here we have also implicitly used the uniformity assumption (assumption 3). Now we can estimate $\lambda_1$ and $\lambda_2$ in the usual Bayesian manner. Both $k_1$ and $k_2$ are assumed to obey the Poisson distribution, $$p(k|\lambda) = \frac{\lambda^k}{k!}e^{-\lambda}.$$

Denoting the prior distribution for $\lambda$ by $p_0(\lambda)$, by standard Bayesian reasoning we obtain $$p(\lambda|k) = \frac{p(k|\lambda)p_0(\lambda)}{\int d\lambda p(k|\lambda)p_0(\lambda)}.$$

Assuming from now on a flat prior distribution of $\lambda$, $p_0(\lambda)$ =const, we obtain $$p(\lambda|k) = p(k|\lambda) = \frac{\lambda^k}{k!}e^{-\lambda}.$$

Eventually, $$P(\text{class } 1) = \int_0^\infty d\lambda_1 \int_0^\infty d\lambda_2 \frac{\lambda_1}{\lambda_1 + (N_1/N_2)\lambda_2} p_1(\lambda_1)p_2(\lambda_2),$$

where $$p_1(\lambda_1) = \frac{\lambda_1^{k_1}}{k_1!}e^{-\lambda_1}, p_2(\lambda_2) = \frac{\lambda_2^{k_2}}{k_2!}e^{-\lambda_2}.$$

Computation of this integral gives $$P(\text{class } 1) = \frac{k_1+1}{k_1+k_2+2} \cdot {}_2F_1\left(1, k_2+1; k_1+k_2+3; 1-\frac{N_1}{N_2}\right). \quad (1)$$

where ${}_2F_1(1, k_2+1; k_1+k_2+3; 1-N1/N2)$ is a calculation of the hypergeometric function ${}_2F_1$. The ${}_2F_1$ hypergeometric function is known to persons skilled in this art and is described, e.g., in Handbook of Mathematical Functions, Ed. M. Abramowitz and I. A. Stegun, Dover, N.Y., 1965, see Chapter 15, which is incorporated by reference herein. The definition of the ${}_2F_1$ function is given in section 15.1.1 on page 556 of the Handbook of Mathematical Functions. The function is also described in open source mathematics libraries, including algorithms for calculating this function. Free code for calculating the $_2F_1$ function is available at http://www.netlib.org/cephes/ Corresponding documentation is available at http://www.netlib.org/cephes/doubldoc.html#hyp2f1. This code and the corresponding documentation is also incorporated by reference herein.

Equation (1) is our main result for calculating a probability that a test object belongs to a given class, and can be used in the situation where $N_1$ and $N_2$ are the same, or when they are different. For equal sample sizes in the training set ($N_1=N_2$) this simplifies to the following:

$$P(\text{class } 1) = \frac{k_1 + 1}{k_1 + k_2 + 2}, \frac{P(\text{class } 1)}{P(\text{class } 2)} = \frac{k_1 + 1}{k_2 + 1}. \quad (2)$$

For the situation in which there are more than two classes and sample sizes in the training set are different (i.e., the numbers $N_i$ of objects in each of the classes in the training set are not necessarily the same), it is difficult to obtain p(class i) in closed form. In this case, the following much simplified estimate may be used:

$$\frac{p(\text{class } i)}{p(\text{class } j)} = \frac{(k_i + 1)}{(k_j + 1)} \cdot \frac{N_j}{N_i}$$

Or, equivalently, each p(class i) is proportional to $$\frac{1}{N_i}(k_i + 1), \text{ while } \sum_{i=1}^{N\text{classes}} p(\text{class } i) = 1$$

Once the probabilities for each of the classes are calculated, the computer system (202, FIG. 2) performing classification of the test instance classifies the test instance to the class with the highest estimated probability. Furthermore, the classifier can then make comparisons between such probabilities. For example, a parameter characterizing the confidence of classification is a user-supplied parameter, p-diff, that defines how different the class probabilities have to be in order to assign a test instance to one of the classes. For example, if p-diff is set to 0.1 and the probability for class 1 is 0.6 and for class 2 is 0.4, then the difference is 0.2 and is greater than 0.1, thus the test instance (spectrum) is assigned to class 1. If, on the other hand the class probability for class 1 is 0.52 and for class 2 is 0.48, then the difference is 0.04, which is smaller than 0.1, thus the classifier returns a class label as being "Undefined." The value of the user-supplied parameter, p-diff, may of course vary and take on some other value, such as 0.25 or 0.3. The value that is selected for particular application may depend on the requirements for the confidence of classification.

While the modified, probabilistic KNN algorithm disclosed above may be utilized as the classification algorithm, it can be used in conjunction with other alternative classification algorithms, e.g., as a check of the robustness of the classification produced by the other classification or clustering algorithm. Such algorithms may include fuzzy KNN, Kernel methods (e.g., SVM), spectral clustering, kernel PCA, non-parametric clustering, k-Means, k-Histograms, hierarchical clustering, and random forests, for example.

Unlike the estimates of the overall error rate of kNN classification that depend on the probability distributions associated with the classes, the general result of equation (1) provides an estimate of the reliability of class assignment for each individual test instance, depending only on the (known) training set data. It also properly accounts for complications arising when the numbers of training instances in the two classes are different, i.e. $N_1 \neq N_2$.

B. Probability Estimate Within the kNN Framework

The above section describes a probabilistic classifier which operates in a defined region around the test spectrum, in which this defined region is obtained in the fixed-ω framework. This section will demonstrate that the defined region can be defined for a fixed value of k, i.e. in the proper kNN framework. For each of the k nearest neighbors to the test spectrum, we have the probability $$\tilde{p}_1 \equiv P(\text{neighbor belongs to class } 1) \quad (3)$$

$$= \frac{N_1 \int_\omega p_1(\vec{x}) d\vec{x}}{N_1 \int_\omega p_1(\vec{x}) d\vec{x} + N_2 \int_\omega p_2(\vec{x}) d\vec{x}}.$$

Then $$P(k_1 \text{ of } kNN \text{ belong to class } 1 \mid \tilde{p}_1) = \binom{k}{k_1} \tilde{p}_1^{k_1}(1 - \tilde{p}_1)^{k-k_1},$$

where NN stands for "nearest neighbors". Thus $$P(\tilde{p}_1 \mid k_1 \text{ of } kNN \text{ belong to class } 1) == \quad (4)$$

$$\frac{P(k_1 \text{ of } kNN \text{ belong to class } 1 \mid \tilde{p}_1)P_0(\tilde{p}_1)}{\int P(k_1 \text{ of } kNN \text{ belong to class } 1 \mid \tilde{p}_1)P_0(\tilde{p}_1)d\tilde{p}_1} =$$

$$\frac{\binom{k}{k_1} \tilde{p}_1^{k_1}(1 - \tilde{p}_1)^{k-k_1}}{\int_0^1 \binom{k}{k_1} \tilde{p}_1^{k_1}(1 - \tilde{p}_1)^{k-k_1} d\tilde{p}_1} = (k+1)\binom{k}{k_1} \tilde{p}_1^{k_1}(1 - \tilde{p}_1)^{k-k_1},$$

where we have again assumed a flat prior distribution of $\tilde{p}_1$: $P_0(\tilde{p}_1)$=const. From (3) we obtain $$\frac{\int_\omega p_2(\vec{x}) d\vec{x}}{\int_\omega p_1(\vec{x}) d\vec{x}} = \frac{N_1}{N_2}\left(\frac{1}{\tilde{p}_1} - 1\right).$$

Then for given $\tilde{p}_1$ the probability that the test point belongs to class 1 is $$P(\text{class } 1) = \frac{1}{1 + \frac{\int_\omega p_2(\vec{x}) d\vec{x}}{\int_\omega p_1(\vec{x}) d\vec{x}}} = \frac{N_2 \tilde{p}_1}{N_2 \tilde{p}_1 + N_1(1 - \tilde{p}_1)}.$$

Finally, using (4), $$P(\text{class } 1) = \int_0^1 \frac{N_2 x}{N_2 x + N_1(1-x)}(k+1)\binom{k}{k_1} x^{k_1}(1-x)^{k-k_1} dx \quad (5)$$

$$= \frac{k_1 + 1}{k_1 + k_2 + 2} \cdot {}_2F_1\left(1, k_2 + 1; k_1 + k_2 + 3; 1 - \frac{N_1}{N_2}\right),$$

which is identical to the result (1) obtained in the previous section.

As noted above, the probabilistic classifier is applicable in a variety of contexts, and the disclosed embodiments are offered by way of illustration and not limitation. For example, the methods may be used to classify different types of test instances besides MS data, or used for different diagnostic or prognostic purposes besides those described herein. Additionally, the test data can be obtained from other types of liquids or tissue samples besides serum.

From the foregoing, it will be appreciated that a system has been described for classification of a test instance (FIG. 4, 1106), comprising:

a machine-readable storage device (218) storing a training set (FIG. 4, 400) comprising a plurality of objects (402, 404), each of the objects in the training set being assigned as a member of a class, collectively the objects in the training set comprising members of at least two classes (see FIG. 4); and a computer system (210 FIG. 2) coupled to the machine-readable storage device (218) configured as a probabilistic classifier, the classifier estimating the probability of the test instance as being a member of each class in the training set, the module estimating the probability with reference to the class assignments of k objects in the training set which are neighbors to the test instance within a defined region within the training set. The defined region within the training set may take the form of a sphere ω centered about the test instance 1106 (FIG. 2), and wherein there are $k_1$ neighbors in class 1 within ω and there are $k_2$ neighbors in class 2 within ω. The size of sphere ω is preferably selected such that probability density for classes 1 and 2 are approximately constant within the sphere ω. Alternatively, the defined region used by the probabilistic classifier comprises a set of k objects within the training set which are the k closest objects to the test instance.

In the situation where the training set 400 is composed of objects in two classes, class 1 and class 2, and each of the two classes have the same number N of members in the training set, the computer system is programmed to determine the probability of the test instance being a member of Class 1 by the relation:

$$P(\text{class } 1) = (k_1+1)/(k_1+k_2+2)$$

and wherein the computer system is programmed to determine the probability of the test instance being a member of Class 2 by the relation:

$$P(\text{class } 2) = (k_2+1)/(k_1+k_2+2)$$

where $k_1$ represents the number of neighbors of class 1 within the defined region and $k_2$ represents the number of neighbors in class 2 within the defined region.

In the event that the training set comprises objects being members of two classes, class 1 and class 2, the computer system is programmed to determine the probability of the test instance being a member of class 1 according to the relation:

$$P(\text{class } 1) = \frac{k_1+1}{k_1+k_2+2} \cdot {}_2F_1\left(1, k_2+1; k_1+k_2+3; 1-\frac{N_1}{N_2}\right).$$

where $_2F_1(1, k_2+1; k_1+k_2+3; 1-N_1/N_2)$ is a calculation of the hypergeometric function $_2F_1$. This result can be used both when classes 1 and 2 in the training set have the same number of objects $N_1$ and $N_2$, respectively, in the training set, or when $N_1$ and $N_2$ are different.

When there are at least three classes in the training set and $N_1$ and $N_2$ are different, the probability p(class i) of the test instance being a member of class i in the training set is approximated as being proportional to the expression:

$$\frac{1}{N_i}(k_i+1), \text{ while } \sum_{i=1}^{Nclasses} p(\text{class } i) = 1$$

When there are at least three classes in the training set and $N_1$ and $N_2$ are different, the ratio of the probabilities of the test instance being a member of class i in the training set and class j in the training set is approximated by the relation:

$$\frac{p(\text{class } i)}{p(\text{class } j)} = \frac{(k_i+1)}{(k_j+1)} \cdot \frac{N_j}{N_i}$$

where $N_j$ is the number of objects in class j and $N_i$ is the number of objects in class i.

The objects in the training set can take the form of data sets obtained from two classes of patients: 1) a first class of patients exhibiting an adverse health condition, e.g. cancer or other disease and 2) a second class of patients that do not exhibit the adverse health condition. The classes assigned to the data sets in the training set correspond to the two classes of patients. In this embodiment, the probabilistic classifier is used to classify the patient as either having or not having the adverse health condition. As another example, the data sets in the training set are obtained from two classes of patients: 1) a first class of patients that derive benefit from a particular therapy for treatment of a health condition (e.g., patents that derive benefit from the EGFR drugs in treatment of non-small cell lung cancer) and 2) a second class of patients that do not derive benefit from the said therapy. The classes assigned to the data sets in the training set correspond to the two classes of patients.

Thus, the above detailed description is not intended to be limiting in scope. Persons of skill in this art will immediately envisage the methods and variations used to implement this invention in other areas than those described in detail. All questions regarding scope of the invention are to be answered by reference to the appended claims.

We claim:

1. A system for classification of a test object, comprising:

a machine-readable storage device storing a training set comprising a plurality of objects, each of the objects being assigned as a member of a class, collectively the objects in the training set comprising members of at least two classes; and a computer system coupled to the machine-readable storage device configured as a probabilistic classifier, the probabilistic classifier estimating the probability of the test object as being a member of each of the classes in the training set, wherein the probabilistic classifier estimates the probabilities with reference to the class assignments of objects in the training set which are neighbors to the test object within a defined region within the training set; and wherein the training set comprises objects being members of two classes, class 1 and class 2, wherein classes 1 and 2 in the training set have $N_1$ and $N_2$ numbers of objects respectively, in the training set and wherein the computer system is programmed to determine the probability P(class 1) of the object being a member of class 1 according to the relation:

$$P(\text{class } 1) = \frac{k_1 + 1}{k_1 + k_2 + 2} \cdot {}_2F_1\left(1, k_2 + 1; k_1 + k_2 + 3; 1 - \frac{N_1}{N_2}\right)$$

where $_2F_1(1, k_2+1; k_1+k_2+3; 1-N1/N2)$ is a calculation of the hypergeometric function $_2F_1$ and where $k_1$ represents the number of neighbors of class 1 within the defined region and $k_2$ represents the number of neighbors in class 2 within the defined region.

2. The system of claim 1, wherein the defined region within the training set comprises a sphere $\omega$ centered about the test instance, and wherein there are $k_1$ neighbors of class 1 within $\omega$ and there are $k_2$ neighbors in class 2 within $\omega$.

3. The system of claim 2, wherein the size of sphere $\omega$ is selected such that probability density for classes 1 and 2 are approximately constant within sphere $\omega$.

4. The system of claim 1, where the computer system is further configured to compare the estimated probabilities for each of the classes to determine if the difference in estimated probability between the class having the highest probability estimate and the class having the next highest probability estimate is greater than a user-supplied parameter.

5. The system of claim 4, wherein the user-supplied parameter is 0.1.

6. The system of claim 1, wherein the probabilistic classifier comprises a probabilistic k nearest neighbor classifier.

7. The system of claim 1, wherein the defined region comprises a set of k objects within the training set which are the k closest objects to the test object.

8. The system of claim 1, wherein the objects comprise the intensities of one or more features and/or one or more peaks in mass spectrometry data.

9. The system of claim 8, wherein the objects in the training set comprise test data obtained from two classes of patients: 1) a first class of patients exhibiting an adverse health condition and 2) a second class of patients that do not exhibit the adverse health condition, and wherein the classes assigned to the objects correspond to the two classes of patients.

10. The system of claim 8, wherein the objects in the training set comprise the data obtained from two classes of patients: 1) a first class of patients that derive benefit from a particular therapy for treatment of a health condition and 2) a second class of patients that either do not derive benefit, or suffer adverse effects from the particular therapy for treatment of the medical condition, and wherein the classes assigned to the objects correspond to the two classes of patients.

11. The system of claim 10, wherein the health condition comprises cancer.

12. The system of claim 11, wherein the cancer comprises non-small cell lung cancer.

13. A method for classifying a test object, comprising the steps of:
   accessing a machine-readable storage device storing a training set comprising a number of objects, each of the objects being assigned as a member of a class, collectively the objects in the training set comprising members of at least two classes; and
   estimating the probability of an object as being a member of each class in the training set, the estimating being performed with reference to the class assignments of the objects in the training set which are neighbors to the test object within a defined region within the training set, and classifying the test object as belonging to the class with the highest estimated probability;
   wherein the training set comprises objects being members of two classes, class 1 and class 2, wherein classes 1 and 2 have numbers of objects $N_1$ and $N_2$, respectively, in the training set, and wherein the probability P(class 1) of the test instance being a member of Class 1 is estimated according to the relation:

$$P(\text{class } 1) = \frac{k_1 + 1}{k_1 + k_2 + 2} \cdot {}_2F_1\left(1, k_2 + 1; k_1 + k_2 + 3; 1 - \frac{N_1}{N_2}\right)$$

where $_2F_1(1, k_2+1; k_1+k_2+3; 1-N1/N2)$ is a calculation of the hypergeometric function $_2F_1$ and where $k_1$ represents the number of neighbors of class 1 within the defined region and $k_2$ represents the number of neighbors in class 2 within the defined region.

14. The method of claim 13, further comprising the step of comparing the estimates of probabilities for each of the classes to determine if the difference of estimated probability between the class having the highest probability estimate and the class having the next highest probability estimate is greater than a user-supplied parameter.

15. The method of claim 14, wherein the user-supplied parameter is 0.1.

16. The method of claim 13, wherein the defined region within the training set comprises a sphere $\omega$ centered about the test object, and wherein there are $k_1$ neighbors of class 1 within $\omega$ and there are $k_2$ neighbors in class 2 within $\omega$.

17. The method of claim 16, wherein the size of sphere $\omega$ is selected such that probability density for classes 1 and 2 are approximately constant within sphere $\omega$.

18. The method of claim 13, wherein the defined region comprises a set of k objects within the training set which are the k closest objects to the test instance.

19. The method of claim 13, wherein the objects comprise the intensities of one or more features and/or one or more peaks in mass spectrometry data.

20. The method of claim 19, wherein the objects in the training set comprise test data obtained from two classes of patients: 1) a first class of patients exhibiting an adverse health condition and 2) a second class of patients that do not share the adverse health condition, and wherein the classes assigned to the objects correspond to the two classes of patients.

21. The method of claim 19, wherein the objects in the training set comprise the data obtained from two classes of patients: 1) a first class of patients that derive benefit from a particular therapy for treatment of a health condition and 2) a second class of patients that either do not derive benefit, or suffer adverse effects from the particular therapy for treatment of the health condition, and wherein the classes assigned to the objects correspond to the two classes of patients.

22. The method of claim 21 wherein the health condition comprises cancer.

23. The method of claim 22, wherein the cancer comprises non-small cell lung cancer.

24. A method of classification of a test instance comprising the steps of:
   creating and storing in a machine-readable memory a training set comprising a plurality of objects, the objects being assigned a class label, the objects being members of either class 1 or a class 2;
   obtaining a test instance to be classified;
   classifying the test instance with a computer system configured as a probabilistic classifier by estimating the probability that the test instance is a member of classes 1 and 2, wherein the probability P(class 1) of the test instance being a member of Class 1 is estimated according to the relation:

$$P(\text{class } 1) = \frac{k_1 + 1}{k_1 + k_2 + 2} \cdot {}_2F_1\left(1, k_2 + 1; k_1 + k_2 + 3; 1 - \frac{N_1}{N_2}\right)$$

where $_2F_1$ (1, $k_2$+1; $k_1$+$k_2$+3; 1−N1/N2) is a calculation of the hypergeometric function $_2F_1$ and where $k_1$ represents the number of neighbors of class 1 within a defined region in the training set and $k_2$ represents the number of neighbors in class 2 within the defined region, $N_1$ is the number of objects in class 1 in the training set, and $N_2$ is the number of objects in class 2 in the training set.

25. The method of claim 24, further comprising the steps of conducting mass spectroscopy on a test sample, wherein the test instance comprises a data set representing a spectrum obtained from the mass spectroscopy.

26. The method of claim 25, wherein the test sample comprises a sample obtained from a human subject.

27. The method of claim 24, further comprising the steps of estimating the probability that the test instance is a member of classes 1 and 2, and comparing the estimates of probabilities for each of the classes to determine if the difference of estimated probability between the class having the highest probability estimate and the class having the next highest probability estimate is greater than a user-supplied parameter.

28. A system for classification of a test object, comprising:
a machine-readable storage device storing a training set comprising a plurality of objects, each of the objects being assigned as a member of a class, collectively the objects in the training set comprising members of at least two classes, including class 1 and class 2; and
a computer system coupled to the machine-readable storage device configured as a probabilistic classifier, the probabilistic classifier estimating the probability of the test object as being a member of a class in the training set, wherein the probabilistic classifier estimates the probability with reference to the class assignments of objects in the training set which are neighbors to the test object within a defined region within the training set;
wherein classes 1 and 2 have $N_1$ and $N_2$ objects, respectively, in the training set, wherein $N_1$ and $N_2$ are not the same; and wherein there are only two classes of objects in the training set, classes 1 and 2, and wherein the probability P(class 1) of the test instance being a member of Class 1 is estimated according to the relation:

$$P(\text{class } 1) = \frac{k_1 + 1}{k_1 + k_2 + 2} \cdot {}_2F_1\left(1, k_2 + 1; k_1 + k_2 + 3; 1 - \frac{N_1}{N_2}\right)$$

where $_2F_1$ (1, $k_2$+1; $k_1$+$k_2$+3; 1−$^{N1}/_{N2}$) is a calculation of the hypergeometric function $_2F_1$ and where $k_1$ represents the number of neighbors of class 1 within a defined region in the training set and $k_2$ represents the number of neighbors in class 2 within the defined region, $N_1$ is the number of objects in class 1 in the training set, and $N_2$ is the number of objects in class 2 in the training set.

29. The system of claim 28, wherein the probabilistic classifier estimates the probability of the test object as being a member of each of the classes in the training set and classifies the test object as belonging to the class with the highest estimated probability.

30. The system of claim 28, wherein the objects in the training set comprise the intensities of one or more features and/or one or more peaks in mass spectrometry data.

31. The system of claim 30, wherein the objects in the training set comprise test data obtained from two classes of patients: 1) a first class of patients exhibiting an adverse health condition and 2) a second class of patients that do not exhibit the adverse health condition, and wherein the classes assigned to the objects correspond to the two classes of patients.

32. The system of claim 30, wherein the objects in the training set comprise the data obtained from two classes of patients: 1) a first class of patients that derive benefit from a particular therapy for treatment of a health condition and 2) a second class of patients that either do not derive benefit, or suffer adverse effects from the particular therapy for treatment of the medical condition, and wherein the classes assigned to the objects correspond to the two classes of patients.

33. The system of claim 32, wherein the health condition comprises cancer.

34. The system of claim 33, wherein the cancer comprises non-small cell lung cancer.

* * * * *